US011993837B2

(12) United States Patent
Pasca et al.

(10) Patent No.: US 11,993,837 B2
(45) Date of Patent: May 28, 2024

(54) PARTICLES FOR CHEMIRESISTOR SENSOR

(71) Applicant: NanoScent Ltd., Mishgav (IL)

(72) Inventors: Yair Pasca, Kiryat Ata (IL); Eran Rom, Misgav (IL)

(73) Assignee: NanoScent Ltd., Mishgav (IL)

(*) Notice: Subject to any disclaimer, the term of this patent is extended or adjusted under 35 U.S.C. 154(b) by 596 days.

(21) Appl. No.: 17/255,439

(22) PCT Filed: May 26, 2019

(86) PCT No.: PCT/IL2019/050591
§ 371 (c)(1),
(2) Date: Dec. 23, 2020

(87) PCT Pub. No.: WO2020/003297
PCT Pub. Date: Jan. 2, 2020

(65) Prior Publication Data
US 2021/0262965 A1  Aug. 26, 2021

Related U.S. Application Data

(60) Provisional application No. 62/689,404, filed on Jun. 25, 2018.

(51) Int. Cl.
*G01N 27/12* (2006.01)
*B22F 1/08* (2022.01)
(Continued)

(52) U.S. Cl.
CPC .................. *C22C 5/00* (2013.01); *B22F 1/08* (2022.01); *B22F 1/102* (2022.01); *B82Y 30/00* (2013.01);
(Continued)

(58) Field of Classification Search
CPC ......... C22C 5/00; C22C 2200/02; B22F 1/08; B22F 1/102; B22F 2301/25;
(Continued)

(56) References Cited

U.S. PATENT DOCUMENTS 7,749,300 B2  7/2010  Chretien
2006/0159921 A1  7/2006  Murthy et al.
(Continued)

FOREIGN PATENT DOCUMENTS

JP  2008-256690 A  10/2008
KR  20160014134  2/2016
(Continued)

OTHER PUBLICATIONS

Clear copy of the "Fabrication and characterisation . . . technique" article; Aug. 21, 2023.*
(Continued)

*Primary Examiner* — Robert R Raevis
(74) *Attorney, Agent, or Firm* — The Roy Gross Law Firm, LLC; Roy Gross

(57) ABSTRACT

The application discloses a particle for chemiresistor sensor. The particle may include: a nanoparticle core made from a conductive material selected from a group consisting of: Ir, Ir-alloy, IrOx, Ru, Ru-alloy, RuOx and any combination thereof and/or any conducting metallic oxide, having a cross section size of at most 100 nm; and a plurality of organic ligands bonded from one side to the nanoparticle core and capable of interacting with a volatile organic compound.

8 Claims, 3 Drawing Sheets

(51) Int. Cl.
    *B22F 1/102*     (2022.01)
    *B82Y 30/00*     (2011.01)
    *C22C 5/00*     (2006.01)
    *G01N 33/00*     (2006.01)
    *B82Y 35/00*     (2011.01)
    *B82Y 40/00*     (2011.01)

(52) U.S. Cl.
CPC ....... *G01N 27/127* (2013.01); *G01N 33/0027* (2013.01); *B22F 2301/25* (2013.01); *B22F 2302/25* (2013.01); *B82Y 35/00* (2013.01); *B82Y 40/00* (2013.01); *C22C 2200/02* (2013.01)

(58) Field of Classification Search
CPC ..... B22F 2302/25; B82Y 30/00; B82Y 35/00; B82Y 40/00; B82Y 15/00; G01N 27/127; G01N 33/0027; G01N 27/3278; G01N 27/407; G01N 33/0047; G01N 33/004
USPC ............. 73/19.01, 23.2, 23.34, 31.05, 31.06, 73/61.41, 61.43; 338/13, 34; 324/691, 324/693, 698; 422/83, 94–97; 977/902, 977/920–922
See application file for complete search history.

(56) References Cited

U.S. PATENT DOCUMENTS

2009/0049890 A1* 2/2009 Zhong .................. G01N 33/497
                                                                                  73/23.3
2012/0156099 A1    6/2012   Zhong et al.
2015/0047417 A1    2/2015   Park et al.
2016/0187280 A1    6/2016   Potyralio et al.
2017/0038326 A1    2/2017   Motayed et al.
2017/0322167 A1   11/2017   Swager et al.
2017/0356869 A1   12/2017   Koenig et al.
2019/0187135 A1*   6/2019   Kim ................. G01N 33/54346

FOREIGN PATENT DOCUMENTS

WO   WO 2010/021777    2/2010
WO      2012/026882 A1   3/2012
WO   WO 2017134247      8/2017

OTHER PUBLICATIONS

Welearegay T.G. et al. Fabrication and characterisation of ligand-functionalised ultrapure monodispersed metal nanoparticle nanoassemblies employing advanced gas deposition technique. Nanotechnology, vol. 29, Issue 6, 2018, Article 065603.

International Search Report of Application No. PCT/IL2019/050591 dated Oct. 10, 2019.

Tesfalem Geremariam Welearegay et al: "Fabrication and characterisation of ligand-functionalised ultrapure monodispersed metal nanoparticle nanoassemblies employing advanced gas deposi tion technique", Nanotechnology, Institute of Physics Publishing, Bristol, GB, vol. 29, No. 6, Jan. 8, 2018 (Jan. 8, 2018), p. 65603, XP020324162.

European Search Report of European Application No. 19826557 dated Feb. 7, 2022.

* cited by examiner

PARTICLES FOR CHEMIRESISTOR SENSOR

CROSS-REFERENCE TO RELATED APPLICATIONS

This application is a National Phase Application of PCT International Application No. PCT/IL2019/050591, International Filing Date May 26, 2019, claiming the benefit of U.S. Provisional Patent Application No. 62/689,404, filed Jun. 25, 2018, which are hereby incorporated by reference.

FIELD OF THE INVENTION

The present invention generally relates to chemiresistor sensors. More particularly, the present invention relates to particles for chemiresistor sensors.

BACKGROUND OF THE INVENTION

Chemiresistor sensors are sensors that can detect the presence of volatile compound (VCs). A chemiresistor sensor includes a material or structure that changes its electrical resistance in response to changes in the nearby chemical environment, for example, due to the presence of VCs. Commercial chemiresistor sensors for sensing VCs include a sensing element made from one of: carbon nanotubes, graphene, carbon nanoparticles, conductive polymers and the like. These chemiresistor sensors are sensitive to cleaning and regeneration cycles which are required after each measurement, due to the nonuniformity nature of the sensor's material. Another optional sensor includes metallic nanoparticles cores coated with organic ligands. The organic ligands are bonded with the surface of the metallic core at one end and are configured to be weakly bonded (e.g., interact) to a VC at the other end. The most suitable and widely used cores are nanoparticles of: Au, Pt, Pd Ag and further also alloys consisting of Ni, Co, Cu, Al, Au/Ag, Au/Cu, Au/Ag/Cu, Au/Pt, Au/Pd, Au/Ag/Cu/Pd, Pt/Rh, Ni/Co, and Pt/Ni/Fe.

The most commonly type of organic ligands that can bond with the surface of a metallic particle having one of the above listed metallic cores is thiol (sulfides). Thiols can be bonded with the metallic cores via groups such as: alkyl-thiols with C3-C24 chains, ω-functionalized alkanethiolates, arenethiolate, (γ-mercaptopropyl) tri-methyloxysilane, dialkyl disulfides, xanthates, oligonucleotides, polynucleotides, peptides, proteins, enzymes, polysaccharides, and phospholipids. These bonds are relatively stable in comparison with other organic ligands, but not stable enough and wear in time.

Chemiresistor sensors must be regenerated prior to taking a new measurement by heating or flushing the sensor with hot air or an inert gas. The heating and/or flushing processes weakens the bond between the thiol and the VC as to allow the VC to be separated from the thiol. However, these heating/flushing cycles further wear and weaken the bonds between the thiols and the metallic cores causing the thiols to disconnect from the surface of the metallic core. Any rise of temperature above ~60° C. weaken the bonds. In addition, the sensor is exposed to ambient oxygen and therefore, in each cycle (whether heated or not) the metal surface will oxidize, and the thiol-surface bond may be prone to degradation or the particle surface itself. This reduces the sensing efficiency and durability of the chemiresistor sensor in time.

Accordingly, there is a need to increase the durability of the sensing element by increasing the strength of the bonds between the organic ligands and the metallic cores or the particle surface itself.

SUMMARY OF THE INVENTION

Some aspects of the invention may relate to a particle for chemiresistor sensor. In some embodiments, the particle may include: a nanoparticle core made from a conductive material selected from a group consisting of: Ir, Ir-alloy, $IrO_x$, Ru, Ru-alloy, $RuO_x$ and any combination thereof, having a cross section size of at most 100 nm; and a plurality of organic ligands bonded from one side to the nanoparticle core and capable of interacting with a volatile organic compound.

In some embodiments, the nanoparticle core may be at least partially covered with an oxide layer comprising at least one of: $IrO_x$ and $RuO_x$. In some embodiments, the organic ligands are selected from a group consisting of: Diazoniums, Silanes, Carboxylic Acids, Tri-chloro, methoxy, ethoxy, Tri hydroxide, di-chloro, chloro and any combination thereof.

In some embodiments, the nanoparticle core has a crystalline structure. In some embodiments, the core has an amorphous structure. In some embodiments, the core has a mixed structure having a first material coated by a second material. In some embodiments, the first material is one of: Ir, Ir-alloy, Ru and Ru-alloy and the second material is one of $IrO_x$ and $RuO_x$.

Some aspects of the invention may may relate to a chemiresistor sensor that may include: two electrodes; and a sensing element electrically connected to the two electrodes and including a structure made from the particles according to any one of the embodiments disclosed herein.

Some aspects of the invention may be related to a particle for chemiresistor sensor. In some embodiments, the particle may include: a nanoparticle core made from a conductive oxide having a cross section size of at most 100 nm; and a plurality of organic ligands bonded from one side to the nanoparticle core and capable of interacting with a volatile organic compound.

In some embodiments, the organic ligands may be selected from a group consisting of: Diazoniums, Silanes, Carboxylic Acids, Tri-chloro, methoxy, ethoxy, Tri hydroxide, di-chloro, chloro and any combination thereof. In some embodiments, the nanoparticle core has a crystalline structure. In some embodiments, the core has an amorphous structure. In some embodiments, the core has a mixed structure having a first material coated by a second material.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1A:
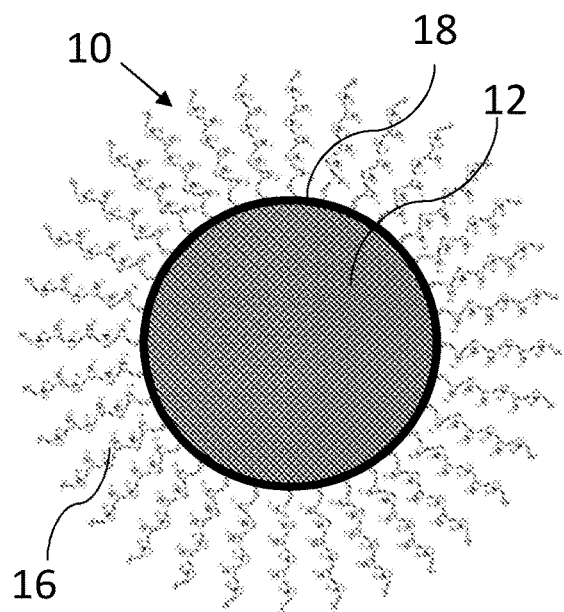
FIGS. 1A-1D are illustrations of particles for chemiresistor sensor according to some embodiments of the invention.
Figure 1B:
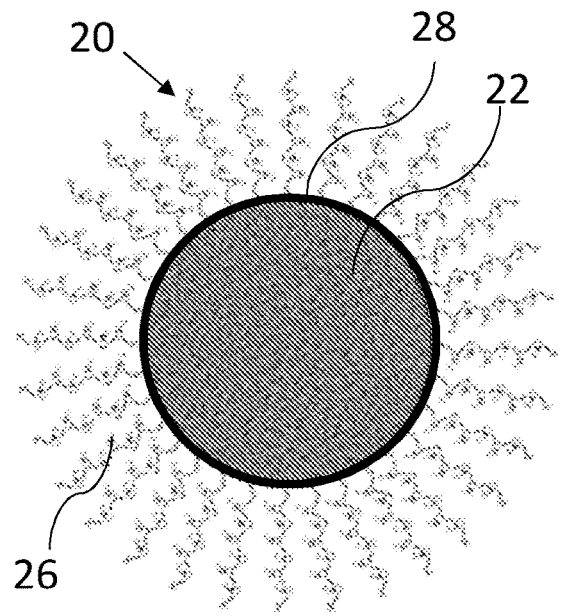
Figure 1C:
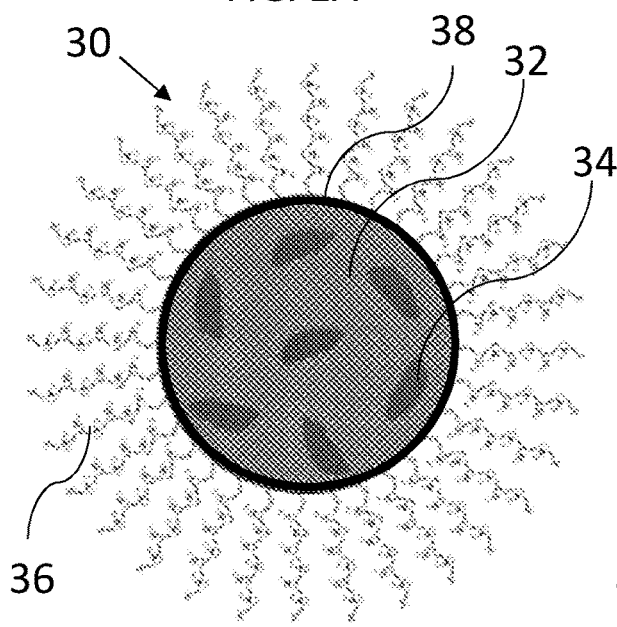
Figure 1D:
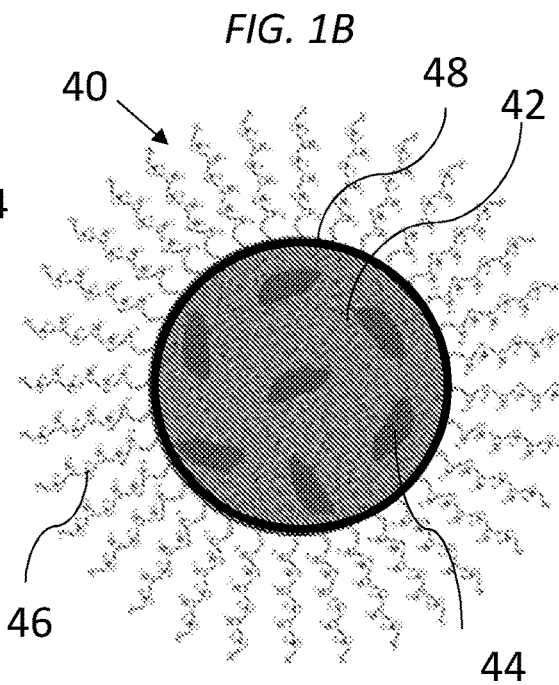

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Aspects of the invention may be directed to particles for chemiresistor sensors. Particles according to some embodiments of the invention may have high durability and may allow extending the operation duration of the chemiresistor sensors over chemiresistor sensors known in the art. For example, a chemiresistor sensor according to embodiments of the invention may last 10,000 cycles at temperatures below 80° C. while the commonly used chemiresistor sensor may last at most 1000 cycles at temperatures below 60° C. At temperatures below 60° C., a chemiresistor sensor according to embodiments of the invention may last 100,000 cycles. Each chemiresistor sensor is subjected to sensing/regeneration cycles each time.

A chemiresistor sensor according to embodiments of the invention may include nanoparticle cores made from novel conductive nanoparticle cores that may include Ir, Ir-alloy, $IrO_x$, Ru, Ru-alloy, $RuO_x$ and any combination thereof. As used herein, an alloy may be defined as a metal that includes a primary metallic element (e.g., Ir and Ru) being the major component (e.g., by wt. %) mixed with any additional element, either metallic or nonmetallic. For example, Ir alloy may include a mixture of Ir being the major component with, Pd, Ru, Au, Pt, Ag and the like and Ru alloy may include a mixture of Ru being the major component with, Pd, Ru, Au, Pt, Ag and the like. In some embodiments, the nanoparticle cores may include any electrically conductive metal oxide, for example, $SrRuO_3$, $CrO_2$, $IrO_x$, $RuO_x$ and the like. In some embodiments, each nanoparticle core may be at least partially covered with an oxide layer comprising at least one of: $IrO_x$ and $RuO_x$. In some embodiments, such an oxide layer may allow bonding additional organic ligands, such as, Diazoniums, Silanes, Carboxylic Acids, Tri-chloro, methoxy, ethoxy, Tri hydroxide, di-chloro, chloro and the like. In some embodiments, these organic ligands may form much stronger bonds with the oxide layer on the nanoparticle core than the bond thiol form on any of the nanoparticle cores listed in the prior art. In some embodiments, the oxide layer may prevent any further oxidation of the core nanoparticle, making the core nanoparticle stable in air (e.g., in the presence of oxygen).

In some embodiments, the bonds formed between the organic ligands and the oxide in the core particle may be stronger than the bonds formed between thiol or any other organic ligand with the metallic surface of any one of the prior art particles. In some embodiments, the bonds formed between the organic ligands and the particle oxide surface in the core particle may include mainly covalent bonds, for example, Ru—O—Si. In some embodiments, the bonds formed between the organic ligands and particle metallic surface, for example, M-S (M is the metal atom) may include partially electrostatic and partially covalent bonds. For example, the for gold particle coated with thiol the strength of the Au—Au—S—C bond dissociation energies may be 221(Au—Au), 418(Au—S), 699(S—C) KJ/mole, respectively, while for $RuO_x$ particle coated with silane the bond dissociation energies of the O—Ru—O—Si bond may be 481(O—Ru), 481(Ru—O), 789(O—Si) KJ/mole, respectively.

In some embodiments, each organic ligand may further include functional groups configured to interact with VCs via hydrogen or Van Der Waals (VDW) bonds. For example, the organic ligands may include OH groups or N groups configured to interact with water. In another example, the organic ligands may include benzene ring configured to interact with aromatic VCs. In yet another example, the organic ligands may include ionic or charged functional groups configured to interact with ionic VC, such as acids (e.g., citric acid, etc.).

Reference is now made to FIGS. 1A-1D which are illustrations of particles for a chemiresistor sensor according to some embodiments, of the invention. In some embodiments, each one of particles 10, 20, 30 and 40 may include: a nanoparticle core 12, 22, 32 and 42 respectively. Nanoparticle cores 12-42 may be made from a conductive material selected from a group consisting of of: Ir, Ir-alloy, $IrO_x$, Ru, Ru-alloy, $RuO_x$ and any combination thereof. In some embodiments, nanoparticle cores 12-42 may be made from any conductive metallic oxide. In some embodiments, the average cross section size of nanoparticle cores 12-42 may be of at most 100 nm, for example, 50 nm, 20 nm, 10 nm, 5 nm and 1 nm.

In some embodiments, nanoparticle core 12 may include a single metal or alloy and may have crystalline structure. In some embodiments, nanoparticle core 22 may include a single metal or alloy and may have an amorphous structure. In some embodiments, nanoparticle cores 32 and 42 may include more than one metal or alloy, for example, nanoparticle cores 32 and 42 may include a crystallin and amorphous matrixes 33 and 43 respectively form a first material (e.g., a conductive oxide such as $RuO_x$, $IrO_x$) and one or more particles 34 and 44 from a second material (e.g., Ru alloy, Ru, Ir alloy, Ir). In some embodiments, matrix 33 may have a crystalline structure and matrix 43 may have an amorphous structure.

Figure 2:
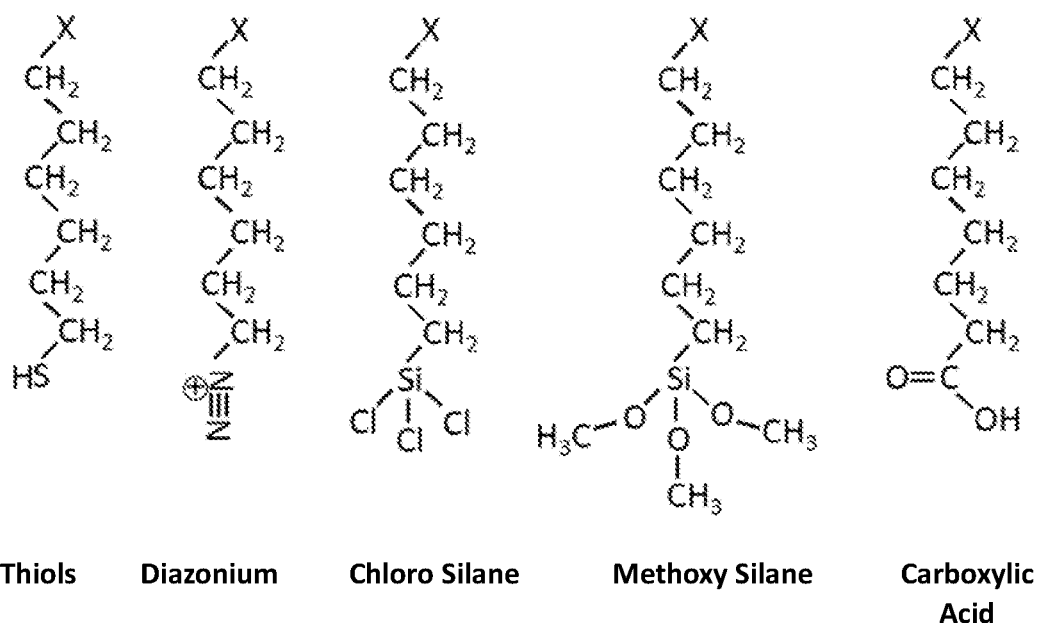
FIG. 2 is table illustrating optional ligands according to embodiments of the invention.

In some embodiments, each one of particles 10, 20, 30 and 40 may further include a plurality of organic ligands 16, 26, 36 and 46, respectively, bonded, for example, via covalent bonds, from one side to the metallic core and capable of interacting with a volatile organic compound. In some embodiments, the organic ligands are selected from a group consisting of: thiols, diazoniums, silanes, carboxylic acids, tri-chloro, methoxy, ethoxy, tri hydroxide, di-chloro, chloro and the like. In some embodiments, more than one type of organic ligand may be bonded with one of cores 10-40. For example, a core 10 that includes crystalline $RuO_x$ may be coated with organic ligands 16 of methoxy silane and trichloro silane. Some examples for organic ligands according to some embodiments of the invention are given in the table of FIG. 2. The organic ligands presented in FIG. 3 can bond from one side with the surface of cores 10-14. For example, the side that includes the bonding group, (e.g., the chloro-silane, group) may covalently bond with atoms on the surface of cores 10-14. In some embodiments, the organic ligands may bond from the other side (marked as X) with a VC, for example, a specific functional group can be added to the ligand chain that is configured to target (e.g., interact with) to a specific VC. In some embodiments, the VC may interact with the branch of the organic ligands, for example, via VDW or hydrogen bonds.

In some embodiments, nanoparticle cores 10-40 may be at least partially covered with an oxide layer 18, 28, 38 and 48 respectively, including at least one of: $IrO_x$ and $RuO_x$ or any other conductive oxides. In some embodiments, when nanoparticle cores 10-40 include crystalline or amorphous Ir, Ir-alloy, Ru and Ru-alloy, a thin oxidation layer may form on at least a portion of the surface of nanoparticle cores 10-40. The thin oxidation layer may be formed due to the exposure of the nanoparticle cores to air or oxygen. The thickness of the oxidation layer may be of few nanometers, for example, a native oxide layer of 1-2 nm. In some embodiments, such an oxidation layer may allow stronger bonding between organic ligand 16-46 and the surface of cores 10-40.

Figure 3:
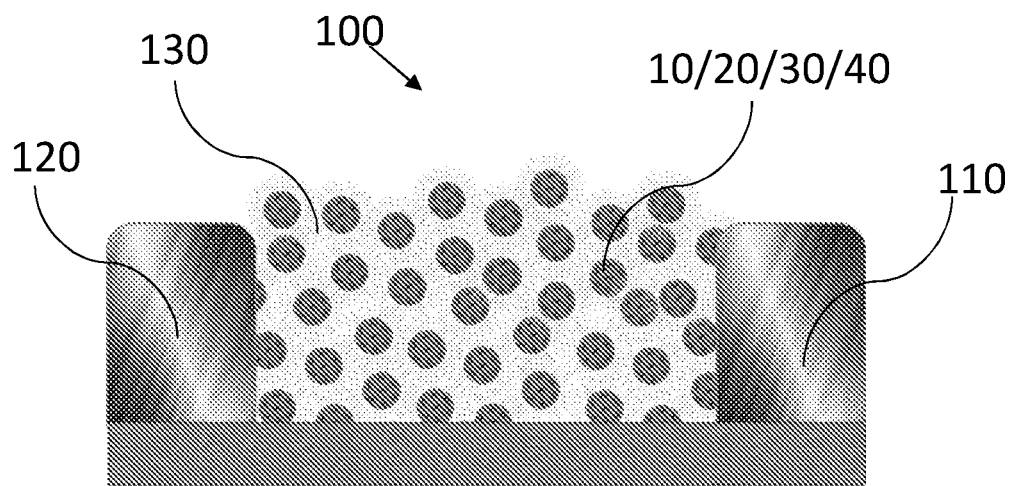
FIG. 3 is an illusration of chemiresistor sensor according to some embodiments of the invention.

Reference is now made to FIG. 3 which is an illusration of a chemiresistor sensor according to som25oCe embodiments of the invention. A chemiresistor sensor 100 may include: two electrodes 110 and 120 and a sensing element 130 connected to electrodes 110 and 120 and comprising a structure made from the particles 10-40 discloses herein.

Figure 4:
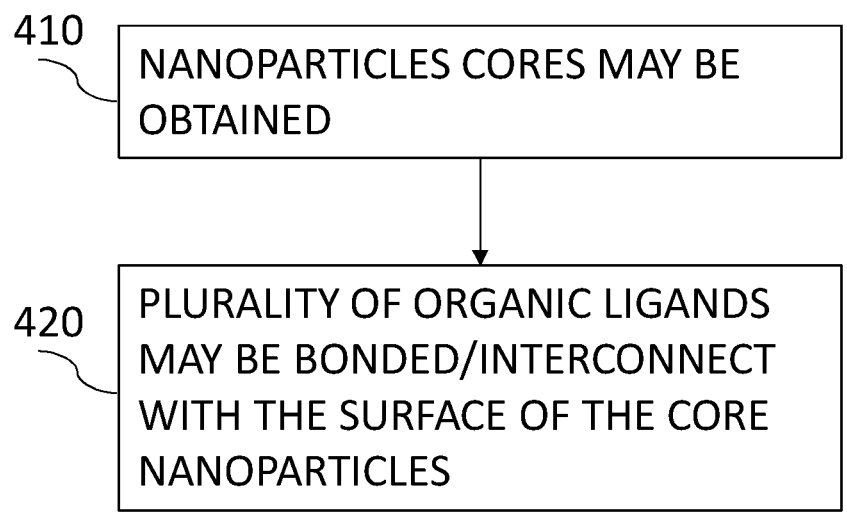
FIG. 4 is a flowchart of a method of making particles for chemiresistor sensor according to some embodiments of the invention.

Reference is now made to FIG. 4 which is a flowchart of a method of making particles for chemiresistor sensor according to some embodiments of the invention. In step 410, nanoparticles cores (e.g., cores 12, 22, 32 and 42) made from a conductive material selected from a group consisting of: Ir, Ir-alloy, $IrO_x$, Ru, Ru-alloy, $RuO_x$, or any conductive metal oxide may be obtained. In some embodiments, the nanoparticles cores may be commercially available for purchasing, either as crystalline, amorphous and/or as an alloy. In some embodiments, the nanoparticles cores may be prepared by, for example, a co-dispersion, and/or by ball milling and the like.

In some embodiments, the core particles may be prepared by reduction of a salt of the required metal(s), e.g. $RuCl_3 \cdot xH_2O$ or similar, by the use of a suitable reducing agent such as sodium acetate, sodium or other borohydride, hydrazine, or any available known reducing agent. the materials may be held in aqueous solution and heated under reflux conditions or hydrothermal conditions, or by heating by microwave or other direct radiation. In these examples, depending on the process chosen, the metal salt and the reducing agent can be pre-mixed or mixed after heating to a desired temperature. Blending of the reducing agent with the metal salt, possibly with additional treatment such as heating/cooling, may lead to the formation of nucleated metal clusters that develop with time into nanoparticles in the reaction mixture. The growth of these particles may be controlled by one or more of: the type of ligands, reaction time, temperature, and in some cases the presence of surface-active agents (surfactants) or other additives to moderate growth of the particles.

In some embodiments, the rate of the reaction and the temperature may be determined for obtaining a crystalline or amorphous structure. For example, using slow rate (e.g., reducing agent insertion to the reaction) and higher temperature (e.g., 0-25° C.) may result in amorphous structure, while using higher reaction rate and lower temperature (e.g., lower than 0° C.) may result in crystalline structure.

In some embodiments, a core (e.g., cores 32 and 42) having at least two types of materials may be prepared in a single step where salts of both materials are present in the reaction mixture. Such a one-step process (e.g., mixing the salts of different metals together) could lead either to alloys of the various particles, separate particles of each or some of the species, or a mixture thereof.

In step 420, the plurality of organic ligands (e.g., organic ligands 16, 26, 36 and 46) may be bonded (e.g., covalently bonded) with the surface of the core nanoparticles. For example, dry powder core nanoparticles may be mixed with solvents and organic ligands (e.g., thiol, silane, and the like) and stirred together for a predetermined amount of time (e.g., a time period in the range of 0.5-2 hours) at a predetermined temperature (e.g., a temperature in the range of 10-40° C.). In some embodiments, the solvent may be selected from a group consisting of: sodium acetate, sodium borohydride or hydrazine, or any other suitable solvent. In some embodiments, in order to disperse the dry core nanoparticles, methods such as, sonication, ultrasonic methods, homogenizing stirring method (e.g., using blades) and the like and by applied.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

Various embodiments have been presented. Each of these embodiments may of course include features from other embodiments presented, and embodiments not specifically described may include various features described herein.

The invention claimed is:

1. A particle for chemiresistor sensor, comprising:
    a nanoparticle core made from a conductive material selected from a group consisting of: Ir, Ir-alloy, IrOx, Ru, Ru-alloy, RuOx and any combination thereof, having an average diameter of at most 100 nm; and
    a plurality of organic ligands bonded from one side to the nanoparticle core and capable of interacting with a volatile organic compound.

2. The particle of claim 1, wherein the nanoparticle core is at least partially covered with an oxide layer comprising at least one of: IrOx and RuOx.

3. The particle of claim 2, wherein the organic ligands are selected from a group consisting of: Amine like Dodecylamine, Diazoniums, Silanes, Carboxylic Acids, Tri-chloro, methoxy, ethoxy, Tri hydroxide, di-chloro, chloro and any combination thereof.

4. The particle according to claim 1, wherein the nanoparticle core has a crystalline structure.

5. The particle according to claim 1, wherein the core has an amorphous structure.

6. The particle according to claim 1, wherein the core has a mixed structure having a first material coated by a second material.

7. The particle according to claim 1, wherein the first material is one of: Ir, Ir-alloy, Ru and Ru-alloy and the second material is one of IrOx and RuOx.

8. A chemiresistor sensor comprising:
two electrodes; and
a sensing element electrically connected to the two electrodes and comprising a structure made from the particles according to claim 1.

* * * * *